US00PP18638P2

(12) United States Plant Patent
Kanaya

(10) Patent No.: US PP18,638 P2
(45) Date of Patent: Mar. 25, 2008

(54) ***CALIBRACHOA* PLANT NAMED 'SUNBELSUPU'**

(50) Latin Name: ***Calibrachoa* sp.**
Varietal Denomination: Sunbelsupu

(75) Inventor: Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/583,607

(22) Filed: Oct. 19, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Calibrachoa* plant named 'Sunbelsupu', characterized by its upright, outwardly spreading and mounding plant habit; vigorous growth habit; freely branching and flowering plant habit; long flowering period; and purple and violet blue-colored flowers.

1 Drawing Sheet

Botanical designation: *Calibrachoa* sp.
Cultivar denomination: 'Sunbelsupu'.

BACKGROUND OF THE INVENTION

The present invention relates to a new and distinct cultivar of *Calibrachoa,* botanically known as *Calibrachoa* sp. and hereinafter referred to by the name 'Sunbelsupu'.

The new *Calibrachoa* is a product of a planned breeding program conducted by the Inventor in Higashiomi, Shiga, Japan. The objective of the breeding program is to develop new uniform *Calibrachoa* cultivars with attractive and unique flower coloration.

The new *Calibrachoa* originated from a cross-pollination made by the Inventor in April, 2002 in Higashiomi, Shiga, Japan of a proprietary selection of *Calibrachoa* sp. identified as code number 9L82, not patented, as the female, or seed, parent with a proprietary selection of *Calibrachoa* sp. identified as code number 9L68, not patented, as the male, or pollen, parent. The new *Calibrachoa* was discovered and selected by the Inventor as a single flowering plant within the progeny of the stated cross-pollination in a controlled environment in Higashiomi, Shiga, Japan.

Asexual reproduction of the new *Calibrachoa* by terminal cuttings in a controlled environment in Higashiomi, Shiga, Japan since September, 2004, has shown that the unique features of this new *Calibrachoa* are stable and reproduced true to type in successive generations.

SUMMARY OF THE INVENTION

The cultivar Sunbelsupu has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunbelsupu'. These characteristics in combination distinguish 'Sunbelsupu' as a new and distinct cultivar of *Calibrachoa:*

1. Upright, outwardly spreading and mounding plant habit.

2. Vigorous growth habit.
3. Freely branching and flowering plant habit.
4. Long flowering period.
5. Purple and violet blue-colored flowers.

Plants of the new *Calibrachoa* can be compared to plants of the parent selections. Plants of the new *Calibrachoa* differ from plants of the parent selections in the following characteristics:

1. Plants of the new *Calibrachoa* have smaller flowers than plants of the parent selections.
2. Petals of plants of the new *Calibrachoa* were not as rounded as petals of plants of the parent selections.
3. Plants of the new *Calibrachoa* and the parent selections differ in flower color as plants of the parent selections have darker colored flowers.

Plants of the new *Calibrachoa* can also be compared to plants of the cultivar Sunbelfire, disclosed in U.S. Plant Pat. No. 16,684. In side-by-side comparisons conducted in Higashiomi, Shiga, Japan, plants of the new *Calibrachoa* and the cultivar Sunbelfire differed in the following characteristics:

1. Plants of the new *Calibrachoa* had larger flowers than plants of the cultivar Sunbelfire.
2. Plants of the new *Calibrachoa* and the cultivar Sunbelfire differed in flower color as plants of the cultivar Sunbelfire had yellow and red bi-colored flowers.
3. Plants of the new *Calibrachoa* had shorter and thicker peduncles than plants of the cultivar Sunbelfire.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelsupu' grown in a container.

The photograph at the bottom of the sheet comprises a close-up of typical flowers of 'Sunbelsupu'.

DETAILED BOTANICAL DESCRIPTION

The aforementioned photographs and following observations, measurements and values describe plants grown in Higashiomi, Shiga, Japan, under commercial practice during the spring in an outdoor nursery. During the production of the plants, day temperatures averaged 21° C. and night temperatures averaged 14° C. Plants were grown for about four months with one plant per 13.5-cm container and pinched one time. In the following description, color references are made to The Royal Horticultural Society Colour Chart, 2001 Edition, except where general terms of ordinary dictionary significance are used.

Botanical classification: *Calibrachoa* sp. cultivar Sunbelsupu.

Parentage:

*Female, or seed, parent.*—Proprietary selection of *Calibrachoa* sp. identified as code number 9L82, not patented.

*Male, or pollen, parent.*—Proprietary selection of *Calibrachoa* sp. identified as code number 9L68, not patented.

Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous; light brown in color.

*Rooting habit.*—Freely branching.

Plant description:

*Plant and growth habit.*—Upright, outwardly spreading and mounding plant habit. Freely branching with lateral branches potentially forming at every node; pinching enhances lateral branch development. Vigorous growth habit.

*Plant height.*—About 15.9 cm.

*Plant diameter.*—About 43.6 cm.

Lateral branch description:

*Length.*—About 16.8 cm.

*Diameter.*—About 1.4 mm.

*Internode length.*—About 7 mm.

*Strength.*—Strong.

*Aspect.*—Initially upright to outward.

*Texture.*—Pubescent.

*Color.*—144B.

Foliage description:

*Arrangement.*—Alternate, simple.

*Length.*—About 3.2 cm.

*Width.*—About 1.1 cm.

*Shape.*—Lanceolate.

*Apex.*—Obtuse.

*Base.*—Cuneate.

*Margin.*—Entire.

*Texture, upper and lower surfaces.*—Pubescent.

*Venation pattern.*—Pinnate; reticulate.

*Color.*—Developing foliage, upper and lower surfaces: 145B. Fully expanded foliage, upper surface: 138A; venation, 137B. Fully expanded foliage, lower surface: 137D; venation, 137C.

*Petiole.*—Length: About 3.6 mm. Diameter: About 0.5 mm. Texture, upper and lower surfaces: Pubescent. Color, upper and lower surfaces: 145B.

Flower description:

*Flower arrangement and habit.*—Single salverform flowers arising from upper leaf axils. Freely flowering habit with usually about two to three open flowers per lateral branch. Flowers not persistent. Flower face upright or outwardly. Flowers not fragrant.

*Natural flowering season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant.

*Flower diameter.*—About 3.6 cm.

*Flower length (depth).*—About 2.5 cm.

*Throat diameter.*—About 7 mm.

*Tube diameter.*—About 2.5 mm.

*Flower bud.*—Shape: Cylindrical. Length: About 2.2 cm. Diameter: About 4.3 mm. Color: Towards the apex, N81C; towards the base, 1C.

*Corolla.*—Arrangement: Five petals fused at the base and opening into a flared trumpet. Petal length from throat: About 1.6 cm. Petal width: About 1.9 cm. Petal shape: Spatulate. Petal apex: Rounded with truncate tendencies. Petal margin: Entire. Petal texture, upper and lower surfaces: Smooth, glabrous; satiny. Color: Petal, when opening, upper surface: 83B. Petal, when opening, lower surface: 84A. Petal, fully opening, upper surface: 91D; towards base, N82A; venation, N82A. Petal, fully opened, lower surface: 84B; venation, 166C. Throat: 13B; venation, 166C. Tube: 16D; venation, 166C.

*Calyx.*—Arrangement: One star-shaped calyx tube with five sepals fused at the base per flower. Sepal length: about 1.3 cm. Sepal width: About 3 mm. Sepal shape: Lanceolate. Sepal apex: Acute. Sepal margin: Entire. Sepal texture, upper and lower surfaces: Pubescent. Color, upper and lower surfaces: 137B.

*Peduncles.*—Length: About 2.3 cm. Diameter: About 8 mm. Angle: About 45° from vertical. Strength: Strong. Texture: Pubescent. Color: N144A.

*Reproductive organs.*—Stamens: Quantity/arrangement: Five per flower. Anther shape: Ellipsoidal. Anther size: About 1 mm by 1 mm. Anther color: 12C. Pollen amount: Moderate. Pollen color: 12D. Pistils: Quantity: One per flower. Pistil length: About 1 cm. Style color: 144C. Stigma shape: Transversely ellipsoidal. Stigma color: 144B. Ovary color: N144C. Seed/fruit: Seed and fruit development have not been observed on plants of the new *Calibrachoa*.

Temperature tolerance: Plants of the new *Calibrachoa* have been observed to tolerate temperatures from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Sunbelsupu' as illustrated and described.

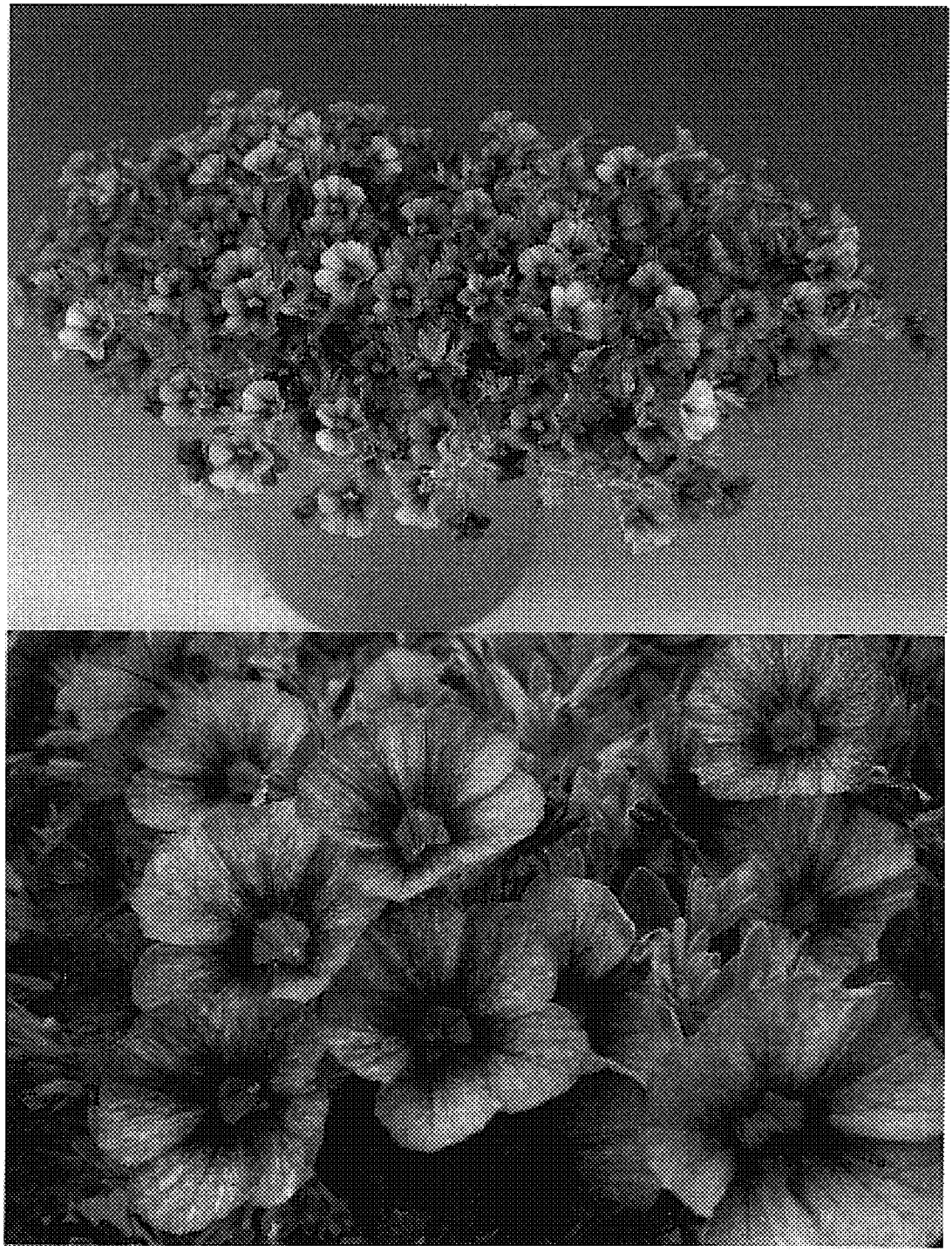

* * * * *